United States Patent [19]

Schönafinger

[11] 4,431,830

[45] Feb. 14, 1984

[54] PROCESS FOR THE PREPARATION OF ISOSORBIDE-5-NITRATE

[75] Inventor: Karl Schönafinger, Uehlfeld, Fed. Rep. of Germany

[73] Assignee: Cassella Aktiengesellschaft, Fed. Rep. of Germany

[21] Appl. No.: 371,221

[22] Filed: Apr. 23, 1982

[30] Foreign Application Priority Data

May 5, 1981 [DE] Fed. Rep. of Germany ....... 3117612

[51] Int. Cl.³ .......................................... C07D 493/04
[52] U.S. Cl. .................................................. 549/464
[58] Field of Search ......................................... 549/464

[56] References Cited

U.S. PATENT DOCUMENTS 4,371,703  2/1983  Stoss ..................................... 549/464

*Primary Examiner*—Henry R. Jiles
*Assistant Examiner*—Bernard Dentz
*Attorney, Agent, or Firm*—Berman, Aisenberg & Platt

[57] ABSTRACT

In a process for preparing isosorbide-5-nitrate, isosorbide is reacted with an aliphatic carboxylic acid, with the formation of an acylation mixture. The acylation mixture is then nitrated, and the resulting nitration mixture is hydrolyzed and/or transesterified in order to split off acyl groups. The product is used in treatment of angina pectoris.

13 Claims, No Drawings

PROCESS FOR THE PREPARATION OF ISOSORBIDE-5-NITRATE

The present invention relates to a process for the preparation of 1,4-3,6-dianhydro-D-sorbit-5-yl nitrate of formula I

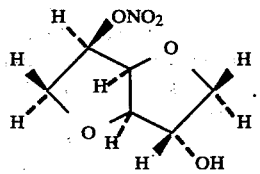

1,4-3,6-Dianhydro-D-sorbit-5-yl nitrate of formula I is also known as isosorbide-5-nitrate or as 5-ISM (isosorbide-5-mononitrate). It is employed as a remedy for treating heart disease, such as Angina pectoris. In the direct nitration of 1,4-3,6-dianhydro-D-sorbitol, also known as isosorbide, by the method of I. G. Csizmadia and D. L. Hayward, Photochem. Photobiol. 4, 657 (1965), a mixture of nitrates is produced in which isosorbide-5-nitrate is present only as a minor constituent. For this reason only low yields of isosorbide-5-nitrate are obtained when isolation is carried out by column chromatography.

In another preparative process, 1,4-3,6-dianhydro-D-sorbit-2,5-diyl dinitrate, also known as isosorbide-2,5-dinitrate, is initially prepared and is then partially saponified. As in the case of the first mentioned process, the individual constituents of the saponification mixture formed, which contains isosorbide-2,5-dinitrate, isosorbide-5-nitrate, isosorbide-2-nitrate and isosorbide, must be separated from one another by involved processes [compare Anteunis et al., "Org. Magnetic Resonance," volume 3, 363 et seq., (1971) and D. L. Hayward et al., Can. J. Chem. 45, 2,191 et seq. (1967)].

In a process for the preparation of 1,4-3,6-dianhydro-D-glucitol mononitrate esters (another name for 1,4-3,6-dianhydro-D-sorbitol mononitrate esters), the isosorbide-2-nitrate and isosorbide-5-nitrate required as starting materials are prepared by the direct nitration of isosorbide (compare German Offenlegungsschrift No. 2,751,934). The nitration mixture is treated with ice water, and the mixture is then extracted with diethyl ether. The ether extract is concentrated while adding water, and the resulting aqueous solution is freeze-dried. Column chromatography of the mixture of nitrates gives isosorbide-5-nitrate in a yield of about 20% by weight.

In a process for the preparation of isosorbide-2-nitrate, which is isomeric with isosorbide-5-nitrate, isosorbide is acylated with a lower alkanoic acid anhydride or chloride or bromide (German Offenlegungsschrift No. 2,903,927), and the isosorbide is then extracted from the acylation mixture in order to prevent, in the subsequent nitration reaction, the formation of isosorbide-2,5-dinitrate, which presents an explosive hazard. In a third stage, the acylation mixture is nitrated, and the resulting mixture of isosorbide-5-acylate-2-nitrate, isosorbide-2-acylate-5-nitrate and isosorbide-2,5-diacylate is hydrolysed by means of an inorganic base. The isosorbide-2-nitrate:isosorbide-5-nitrate ratio in the hydrolysis mixture, consisting of isosorbide-2-nitrate, isosorbide-5-nitrate and isosorbide, is greater than 2:1, that is to say the quantity of isosorbide-2-nitrate is at least twice as great as that of isosorbide-5-nitrate. The isosorbide-2-nitrate is isolated from the hydrolysis mixture by crystallization.

Finally, a process for the preparation of isosorbide-5-nitrate which starts from 1,4-3,6-dianhydromannitol, also known as isomannide, is also known (German Offenlegungsschrift No. 2,903,927). In this process, isomannide is first reacted with an acid halide of an aromatic, optionally-substituted benzenesulphonic or naphthalenesulphonic acid or with an acid halide of a perfluoro-$C_{1-4}$ lower alkanesulphonic acid, of a $C_{1-4}$ lower alkanesulphonic acid or of a perfluoro-$C_{1-4}$ lower alkanecarboxylic acid, or of a carbamic acid or of sulphurous acid. In this process, it is also possible to employ the corresponding anhydrides instead of the acid chlorides, in the case of the sulphonic acid, the perfluoro-$C_{1-4}$ lower alkanesulphonic acid, the $C_{1-4}$ lower alkanesulphonic acid or the perfluoro-$C_{1-4}$ lower alkanecarboxylic acid mentioned. The resulting isomannide-2-ester is then reacted with an alkali-metal salt or ammonium salt of an optionally-substituted benzoic acid or of a $C_{1-4}$ lower alkanecarboxylic acid or of formic acid, the 5-hydroxyl group of the resulting isosorbide-2-ester is esterified with nitric acid, and the resulting isosorbide-2-ester-5-nitrate is selectively hydrolysed and/or transesterified.

The processes hitherto known for the preparation of isosorbide-5-nitrate are multistage, involve tedious and expensive purification operations or only provide the desired product in an unsatisfactory yield or, in addition, require—as in the case of isomannide—starting materials which are not commercially available.

In the process of the present invention, isosorbide-5-nitrate is prepared, starting from isosorbide, in a relatively simple process and in a relatively high yield. In the process according to the invention (for the preparation of 1,4-3,6-dianhydro-D-sorbit-5-yl nitrate of formula I, also known as isosorbide-5-nitrate), 1,4-3,6-dianhydro-D-sorbitol, also known as isosorbide, is reacted with an aliphatic carboxylic acid; the resulting acylation mixture is nitrated; the acyl group is then split off by hydrolysis and/or transesterification; and the isosorbide-5-nitrate is isolated.

Aliphatic carboxylic acids having from 1 to 7 C atoms are normally used for the reaction with isosorbide. The following are examples of aliphatic carboxylic acids of this type: formic acid, acetic acid, propionic acid, butyric acid, isobutyric acid, valeric acid, isovaleric acid, caproic acid or oenanthic acid, and also acrylic acid, methacrylic acid, cis- or trans-crotonic acid, vinylacetic acid or angelic acid or a mixture of said acids. Alkanecarboxylic acids are preferred, particularly those having from 2 to 4 C atoms (acetic acid, propionic acid, butyric acid or isobutyric acid). Acetic acid is preferably used.

The reaction between isosorbide and the aliphatic carboxylic acid is carried out in the absence of a solvent or, preferably, in the presence of a suitable solvent. Preferred solvents are those which have adequate solvent power for isosorbide and, at the same time, make it possible to remove, by azeotropic distillation, water of reaction formed when the isosorbide is esterified with the aliphatic carboxylic acid. The following are examples of preferred solvents of this type: chloroform, carbon tetrachloride, ethylene chloride, chlorobenzene, dimethoxyethane, diethylene glycol dimethyl ether and toluene. Mixtures of different solvents are, alternatively, used, in particular, for example, chlorobenzene and toluene, or ethylene glycol dimethyl ether and toluene.

The reaction of isosorbide with aliphatic carboxylic acid is carried out in the presence of a non-oxidizing catalyst which has an acid reaction. The following are examples of catalysts of this type: sulphonic acids, such as p-toluenesulphonic acid, ethanesulphonic acid or methanesulphonic acid; non-oxidizing mineral acids, such as sulphuric acid, hydrochloric acid, hydrobromic acid or phosphoric acid; and salts with an acid reaction, such as alkali-metal bisulphates, for example sodium bisulphate. Ion exchangers which are in the acid form or polymeric compounds containing acid groups (instead of free acids) are optionally used for this purpose.

As a rule, from 0.1 to 15% by weight, preferably from 2 to 6% by weight, relative to isosorbide, of the acid-esterification catalyst are used. In the reaction of isosorbide with the aliphatic carboxylic acid, the molar ratio between the isosorbide and the aliphatic carboxylic acid optionally varies within wide limits. In particular, when the reaction is carried out in a suitable solvent, to molar ratio of isosorbide:aliphatic carboxylic acid is normally 1:(0.7 to 1.3), preferably 1:(0.8 to 1.2). However, either the isosorbide or the aliphatic carboxylic acid is, alternatively, present in the reaction mixture in a large molar excess, for example from a 2-fold to a 20-fold or an even greater excess. If a large excess of isosorbide is used, the mixture obtained after reaction with the aliphatic carboxylic acid is separated into unreacted isosorbide and acylation product. This is effected, for example, by removing the excess isosorbide from the reaction mixture by extraction with water or by removing the acylation products from the reaction mixture by extraction with a suitable solvent, such as methylene chloride or ethyl acetate.

If a large molar excess of the aliphatic carboxylic acid is used, steps must be taken to prevent the formation of major amounts of isosorbide-diacylate. This is achieved in a simple manner by adding an adequate quantity of a solvent which is suitable for removing the resulting water of reaction by azeotropic distillation and discontinuing the reaction after the theoretical quantity of water has been formed.

The reaction between isosorbide and the aliphatic carboxylic acid is carried out at room temperature or, advantageously, at an elevated temperature, in particular at the reflux temperature of the solvent used. In the course of this, an acylation or esterification of the isosorbide takes place, with the liberation of water. The progress of the reaction can therefore be followed by determining the water liberated. In the acid-catalysed esterification (according to the invention) of isosorbide with aliphatic carboxylic acids, in particular alkanecarboxylic acids having from 1 to 7 C atoms, preferably from 2 to 4 C atoms, surprisingly, virtually no isosorbide-5-acylate is formed; instead the main product formed is isosorbide-2-acylate containing a minor amount of isosorbide-2,5-diacylate as the sole by-product. The isosorbide-2,5-diacylate, which is formed to a minor extent, does not interfere with the progress of the further reaction, but can, if desired, also be removed by distillation or crystallization. The fact that, in the acid-catalysed reaction of isosorbide with aliphatic carboxylic acids, the monoacylate formed is virtually only isosorbide-2-acylate could not have been foreseen, since at least twice as large a quantity (relative to isosorbide-2-acylate) of isosorbide-5-acylate is present in the acylation mixture formed in the acid-catalysed reaction of isosorbide with alkanecarboxylic acid anhydrides or chlorides or bromides (compare German Offenlegungsschrift No. 2,751,934).

The acylation mixture obtained in the acid-catalysed reaction of isosorbide with an aliphatic carboxylic acid, which mixture, besides isosorbide-2-acylate, contains isosorbide-2,5-diacylate as a by-product and not more than traces of isosorbide-5-acylate, is then nitrated in a manner which is in itself known, without further treatment, or, preferably, after removing the isosorbide-2,5-diacylate. This nitration reaction is advantageously carried out in a suitable solvent, such as methylene chloride, at temperatures of from $-10°$ to $30°$ C., preferably from $0°$ to $20°$ C., using a nitration mixture consisting of acetic anhydride/glacial acetic acid/nitric acid or sulphuric acid/nitric acid or acetic acid/nitric acid.

The mixture obtained in the nitration reaction, consisting of isosorbide-2-acylate-5-nitrate and isosorbide-2,5-diacylate, is then hydrolysed and/or trans-esterified (in a manner which is in itself known) without intermediate isolation, whereby isosorbide-5-nitrate is formed as the main product, together with a little isosorbide, by splitting off the acyl groups. The isosorbide is removed without difficulty by extraction with water.

The hydrolysis is most simply carried out with the aid of an aqueous alkali-metal hydroxide solution, for example an aqueous solution of sodium hydroxide, at temperatures of from $0°$ to $50°$ C., preferably from $0°$ to $40°$ C. The transesterification is carried out at temperatures of from $10°$ to $60°$ C., preferably from $20°$ to $60°$ C., in an alcohol, in particular an alcohol having from 1 to 4 C atoms, preferably methanol or ethanol, in the presence of catalytic amounts of a base, for example an alkali-metal hydroxide, such as sodium hydroxide or potassium hydroxide, or of an alkali-metal alcoholate, such as sodium methylate. If aqueous alcohols are used, the transesterification and the hydrolysis proceed side by side.

Before being processed further, it is preferable to isolate the diacylate from the acylation product which is formed in the acid-catalysed reaction of isosorbide with the aliphatic carboxylic acid and which contains isosorbide-2-acylate, isosorbide-2,5-diacylate as a by-product and only traces of isosorbide-5-acylate. This isolation is effected, e.g., by rectification under reduced pressure, for example under a pressure of from 0.05 to 1 mbar, preferably from 0.1 to 0.3 mbar, in the course of which the isosorbide-2-acylate passes over as the first fraction. However, the isosorbide-2-acylate is optionally isolated from the acylation mixture by other means, for example by crystallization. As already described, the isosorbide-2-acylate which has been isolated is then nitrated and subsequently hydrolysed and/or transesterified.

The process according to the invention provides pure isosorbide-5-nitrate in a yield of up to 50%.

The following examples illustrate the process according to the invention.

EXAMPLE 1

An admixture of 146 g of isosorbide, 60 g of glacial acetic acid and 5 g of p-toluenesulphonic acid in 700 ml of ethylene chloride are boiled under reflux, with the interposition of a water separator, until no more water is split off. The reaction mixture is then concentrated; the residue is taken up in 400 ml of methylene chloride and extracted by shaking twice with 100 ml of aqueous concentrated sodium bicarbonate solution. The aqueous phases are extracted by shaking twice with 200 ml of methylene chloride. The methylene chloride phases are combined and dried with sodium sulphate. The methylene chloride solution is then cooled to approximately 10° C. The nitration mixture—prepared by adding 61 g of 100% strength nitric acid dropwise at from −5° to 0° C. to acetic anhydride (108 g) and glacial acetic acid (64 g) which have been cooled to −5° C.—is pre-cooled to −5° C. and is then added dropwise, while stirring, the internal temperature being kept below 20° C. After stirring for a further 2 hours at 20° C., the mixture is poured into approximately 1.2 l of ice water, the organic phase is separated off, the aqueous phase is extracted by shaking once with 200 ml of methylene chloride, and the combined organic phases are extracted by shaking with 300 ml of water and are concentrated (thin-layer chromatography confirms that no explosive isosorbide dinitrate is present). The residue is dissolved in 700 ml of ethanol and warmed to 50° C., a solution of 10 g of potassium hydroxide in 100 ml of ethanol is added, and the mixture is stirred for 10 minutes at 50° C. After cooling to 20° C., the mixture is neutralized with dilute hydrochloric acid and concentrated. The residue is taken up in 500 ml of water and extracted by shaking four times with 100 ml of methylene chloride. The methylene chloride phases are combined, dried over sodium sulphate and concentrated. The residue is recrystallized from a mixture of 3 parts of chloroform and 1 part of carbon tetrachloride and gives 80.2 g of isosorbide-5-nitrate in the form of colorless, felted needles of melting point: 90° to 91° C.

Yield: 42.0% of theory.

EXAMPLE 2

An admixture of 146 g of isosorbide, 80 g of isobutyric acid and 5 ml of concentrated sulphuric acid in a mixture of 400 ml of chlorobenzene and 200 ml of toluene are heated under reflux, with the interposition of a water separator, until no more water is split off. After cooling to 20° C., the mixture is extracted by shaking twice with 300 ml of water, and the combined aqueous phases are extracted by shaking with 200 ml of methylene chloride; the organic phases are combined, dried over sodium sulphate and concentrated. Distillation of this residue under 0.4 mbar gives 115 g of a fraction (boiling at from 117° to 120° C.), which consists of isosorbide-2-isobutylate. This fraction is reacted further, as described in Example 1, and gives 66.7 g of isosorbide-5-nitrate of melting point: 90° to 91° C.

Yield: 34.9%.

EXAMPLE 3

The fraction boiling at from 117° to 120° C./0.4 mbar, as described in Example 2, is added dropwise to a nitration mixture [2.5 g of urea, 64 ml of concentrated nitric acid (D=1.42) and 75 ml of concentrated sulphuric acid] which has been pre-cooled to from 10° to 15° C. The mixture is then stirred at from 15° to 20° C. for 20 minutes and poured into 20 ml of ice water, and the product which separates out is taken up in 400 ml of methylene chloride. After adding 500 ml of toluene, the solution is concentrated to half its volume. 500 ml of 1 N aqueous sodium hydroxide solution are added to this toluene solution, and the mixture is stirred at 20° C. for 18 hours. The aqueous phase is separated off and the toluene phase is diluted with 300 ml of petroleum ether, extracted by shaking once with water and discarded.

The isosorbide-5-nitrate is isolated from the combined aqueous phases by extraction (by shaking with methylene chloride) and by recrystallization from toluene. Melting point: 90° to 91° C.

Yield: 51.3 g (26.9%).

EXAMPLE 4

An admixture of 146 g of isosorbide, 60 g of glacial acetic acid and 5 g of potassium bisulphate in a mixture of 400 ml of diethylene glycol dimethyl ether and 200 ml of toluene are heated under reflux, with the interposition of a water separator, until no more water is split off. The reaction mixture is concentrated under a waterpump vacuum, and the residue is taken up in 400 ml of water and extracted by shaking once with 150 ml of diethyl ether. Isosorbide-2-acetate is then extracted from the aqueous phase by shaking four times with methylene chloride. After the extract has been concentrated, the residue is recrystallized from a little isopropanol. Yield: 109 g of colorless needles; melting point: 77° to 78° C. (57.9% of theory). This product is nitrated and deacetylated (in the manner indicated in Example 1) and provides 91.5 g of isosorbide-5-nitrate of melting point: 90° to 91° C.

Overall yield: 48.0%.

What is claimed is:

1. A process for the preparation of 1,4-3,6-dianhydro-D-sorbit-5-yl nitrate of the formula I

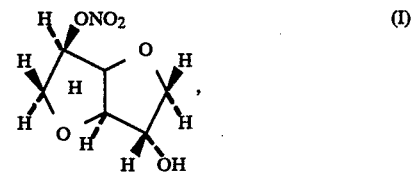

also known as isosorbide-5-nitrate, which comprises (a) reacting 1,4-3,6-dianhydro-D-sorbitol, also known as isosorbide, with an aliphatic carboxylic acid in contact with an acid catalyst to an acylation mixture containing, as the main product, isosorbide-2-acylate, and as a by-product, isosorbide-2,5-diacylate and only traces of isosorbide-5-acylate, (b) nitrating the acylation mixture and (c) hydrolysing and/or transesterifying the resulting nitration mixture in order to split off acyl groups wherein isosorbide-2-acylate is not distilled from the acylation mixture.

2. A process according to claim 1 wherein the aliphatic carboxylic acid has from 1 to 7 C atoms.

3. A process according to claim 1 wherein the aliphatic carboxylic acid is an alkanecarboxylic acid having from 2 to 4 C atoms.

4. A process according to one of claims 1 to 3 wherein the aliphatic carboxylic acid is in contact with a sulphonic acid, a mineral acid or an alkali-metal bisulphate, as an acid catalyst.

5. A process according to one of claims 1 to 3 which comprises reacting isosorbide with the aliphatic carboxylic acid in a solvent, in particular a solvent which is suitable for removing, by azeotropic distillation, the water of reaction formed during the reaction.

6. A process according to one of claims 1 to 3 wherein nitrating is carried out in a solvent at a temperature of from 0° to 20° C.

7. A process according to one of claims 1 to 3 which comprises hydrolysing the resulting nitration mixture with an aqueous alkali-metal hydroxide solution at a temperature of from 0° to 50° C., preferably from 0° to 40° C., in order to split off the acyl groups.

8. A process according to one of claims 1 to 3 which comprises transesterifying the resulting nitration mixture with an alcohol at a temperature of from 10° to 60° C., preferably from 20° to 60° C., in the presence of a catalytic amount of a base in order to split off acyl groups.

9. A process for the preparation of isosorbide-5-nitrate which consists essentially of
   (a) reacting isosorbide with an aliphatic carboxylic acid to obtain the acylation mixture,
   (b) nitrating said acylation mixture and
   (c) hydrolysing and/or transesterifying the resulting nitration mixture.

10. A process for preparing isosorbide-2-acylate-5-nitrate without isolation of isosorbide-2-acylate which comprises nitrating a substantially mono-acylation mixture obtained from an acid catalyzed reaction of isosorbide with an aliphatic carboxylic acid.

11. A process according to claim 10 wherein the acylation mixture, without further treatment, is nitrated.

12. A process according to claim 10 wherein isosorbide-2,5-diacylate is removed from the acylation mixture prior to nitrating.

13. A process according to claim 10 wherein unreacted starting materials are removed from the acylation mixture prior to nitrating.

* * * * *